US008673194B2

(12) United States Patent
Lee et al.

(10) Patent No.: US 8,673,194 B2
(45) Date of Patent: Mar. 18, 2014

(54) METHOD FOR FORMING A CONNECTOR FOR AN IMPLANTABLE MEDICAL DEVICE

(75) Inventors: Nathan T. Lee, Golden Valley, MN (US); Eugene Kuschnir, Forest Lake, MN (US); Jaimie A. Mattson, Ham Lake, MN (US); David A. Bates, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1393 days.

(21) Appl. No.: 12/115,339

(22) Filed: May 5, 2008

(65) Prior Publication Data
US 2008/0303728 A1 Dec. 11, 2008

Related U.S. Application Data

(60) Provisional application No. 60/916,208, filed on May 4, 2007.

(51) Int. Cl.
*B29C 45/14* (2006.01)

(52) U.S. Cl.
USPC ............. 264/250; 264/275; 264/272.15

(58) Field of Classification Search
None
See application file for complete search history.

(56) References Cited

U.S. PATENT DOCUMENTS

| | | | |
|---|---|---|---|
| 4,113,627 A | 9/1978 | Leason | |
| 4,497,756 A * | 2/1985 | Bouchard et al. | 264/1.9 |
| 4,725,395 A * | 2/1988 | Gasparaitis et al. | 264/250 |
| 4,884,980 A | 12/1989 | Bensing et al. | |
| 4,983,344 A | 1/1991 | Brown | |
| 5,098,769 A | 3/1992 | Nakai et al. | |
| 5,453,029 A | 9/1995 | Moldenhauer et al. | |
| 5,861,019 A | 1/1999 | Sun et al. | |
| 5,926,952 A * | 7/1999 | Ito | 29/883 |
| 6,152,761 A * | 11/2000 | Wellinsky et al. | 439/456 |
| 6,205,358 B1 | 3/2001 | Haeg et al. | |
| 6,219,913 B1 | 4/2001 | Uchiyama | |
| 6,256,873 B1 | 7/2001 | Tiffany | |
| 6,338,812 B1 * | 1/2002 | Ogura | 264/254 |
| 6,456,256 B1 | 9/2002 | Amundson et al. | |
| 6,601,296 B1 | 8/2003 | Dailey et al. | |
| 6,708,065 B2 | 3/2004 | Von Arx et al. | |
| 6,817,905 B2 | 11/2004 | Zart et al. | |
| 7,016,733 B2 | 3/2006 | Dublin et al. | |
| 7,047,076 B1 | 5/2006 | Li et al. | |
| 7,103,413 B2 | 9/2006 | Swanson et al. | |
| 7,108,825 B2 | 9/2006 | Dry et al. | |
| 7,601,033 B2 | 10/2009 | Ries et al. | |
| 7,654,843 B2 | 2/2010 | Olson et al. | |
| 7,717,754 B2 | 5/2010 | Ries et al. | |
| 2004/0116976 A1 | 6/2004 | Spadgenske | |
| 2005/0134520 A1 | 6/2005 | Rawat et al. | |
| 2005/0137642 A1 | 6/2005 | Zart et al. | |
| 2005/0203583 A1 | 9/2005 | Twetan et al. | |
| 2005/0203584 A1 | 9/2005 | Twetan et al. | |
| 2005/0244611 A1 * | 11/2005 | Deininger et al. | 428/137 |
| 2005/0245982 A1 | 11/2005 | Kast et al. | |

\* cited by examiner

*Primary Examiner* — Edmund H. Lee
(74) *Attorney, Agent, or Firm* — Carol F. Barry

(57) ABSTRACT

A connector assembly for an implantable medical device with hardware components placed in established physical locations within the polymer of the connector, and a method of making the assembly. One embodiment includes a method that involves forming a first shot, coupling at least one hardware component to the first shot to form a subassembly, placing the subassembly between a set of opposing areas of a mold, moving at least one of the areas of the set of opposed areas of the mold to constrain the subassembly within the mold, and introducing a second shot over at least a portion of the subassembly to form the connector.

13 Claims, 17 Drawing Sheets

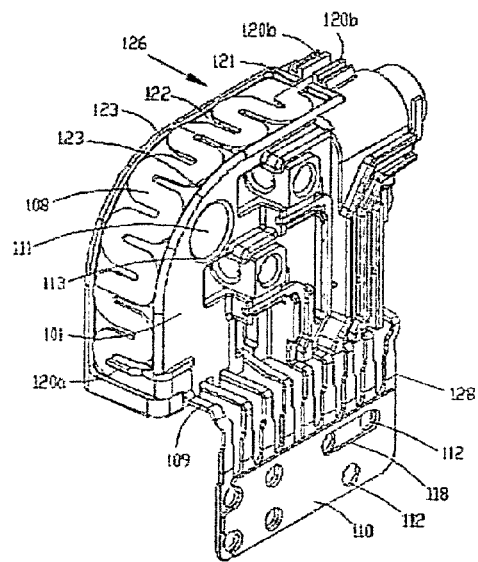
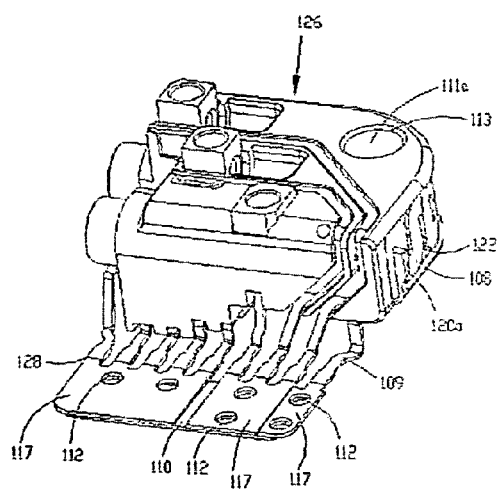
FIG. 16  FIG. 17
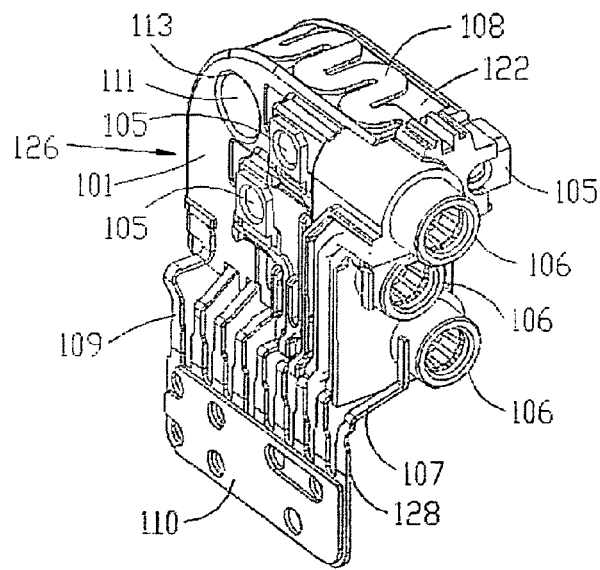
FIG. 18

METHOD FOR FORMING A CONNECTOR FOR AN IMPLANTABLE MEDICAL DEVICE

RELATED APPLICATIONS

This application claims priority to U.S. Provisional Application Ser. No. 60/916,208, filed May 4, 2007, incorporated herein by reference.

TECHNICAL FIELD

This disclosure generally relates to an implantable medical device (IMD), and, more particularly, to a connector that interconnects electronic components housed in the IMD to one or more electrically conductive elements in a medical electrical lead.

BACKGROUND

Implantable medical devices (IMDs) detect and deliver therapy for a variety of medical conditions in patients. The human anatomy includes many types of tissues that can either voluntarily or involuntarily, perform certain functions. After disease, injury, or natural defect, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, implantable pulse generators (IPGs) or combinations thereof.

ICDs typically comprise, inter alia, a control module, a capacitor, a battery that are housed in a hermetically sealed container. A lead is coupled to the container through the connector. When therapy is required by a patient, the control module signals the battery to charge the capacitor, which in turn discharges electrical stimuli to tissue of a patient. IMDs provide therapeutic and/or diagnostic capabilities. It is desirable to develop new IMD components such as a new connector to interconnect the lead to the container.

BRIEF DESCRIPTION OF DRAWINGS

Aspects and features of the present invention will be appreciated and better understood by reference to the following detailed description of the embodiments of the invention when considered in connection with the accompanying drawings, wherein:

FIG. 16 is a perspective view of a subassembly formed of a first component and at least one hardware component.

FIG. 17 is an additional perspective view of the subassembly shown in FIG. 16.

FIG. 18 is an additional perspective view of the subassembly in FIG. 16.

DETAILED DESCRIPTION

The present disclosure relates to a connector that electrically and mechanically couples a medical electrical lead to electronic components in the housing of an implantable medical device (IMD). One embodiment of the connector includes a first component of polymeric material connected to hardware that is then overmolded with polymeric material. The first component includes a pair of opposing areas for securely holding the first component by opposing clamping areas of a mold. The clamping areas allow areas of the mold to hold the first component from opposing sides upon closing of the mold, thereby providing positional stability of the first component and one or more hardware components attached thereto. While the mold securely positions the first component, an encapsulation polymer is then injected over at least a portion of the first component and allowed to cure. Upon curing, the mold can then eject the connector.

Figure 1:
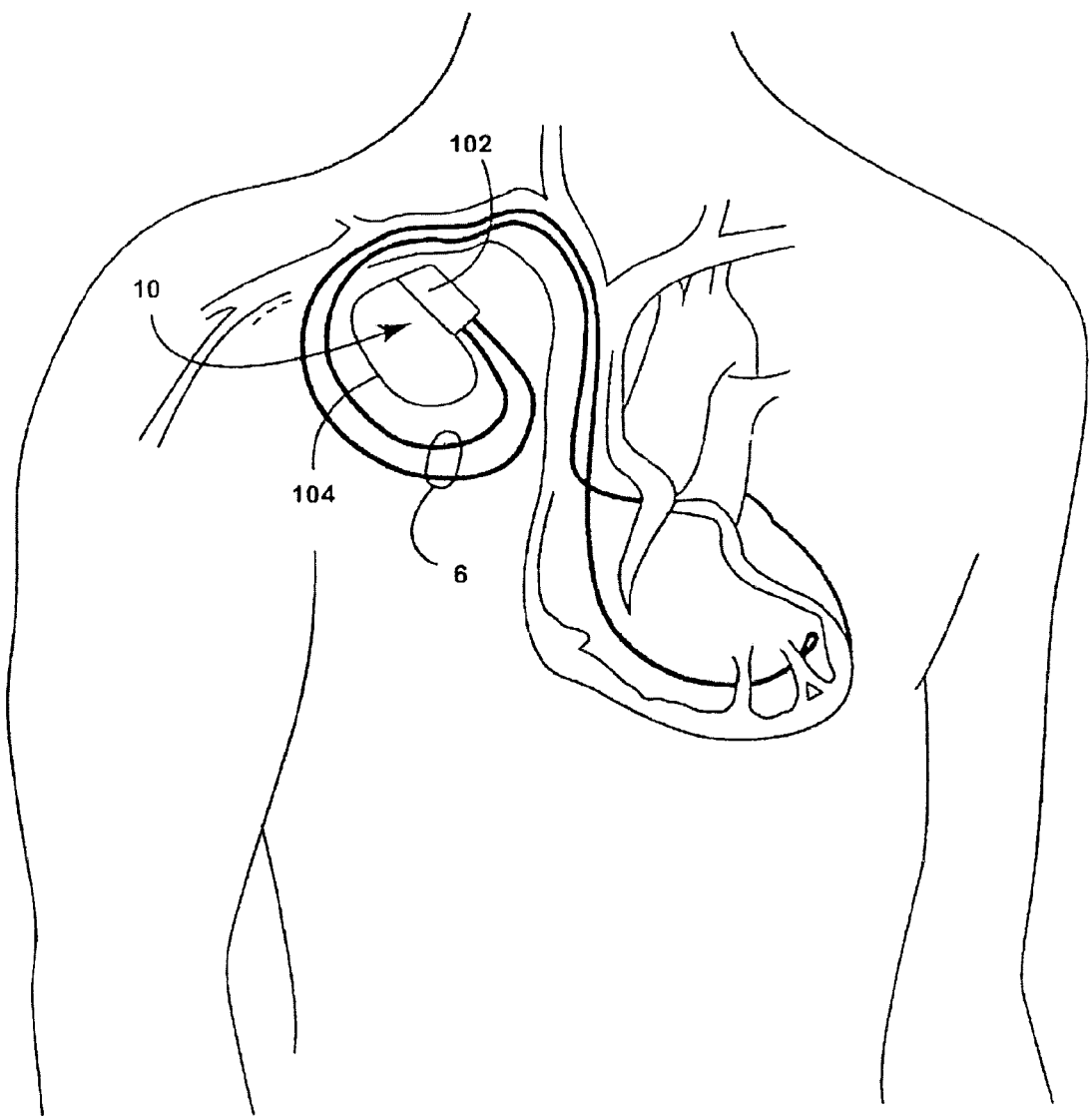
FIG. 1 is system view of an exemplary implantable medical device for a cardiac application.
Figure 2:
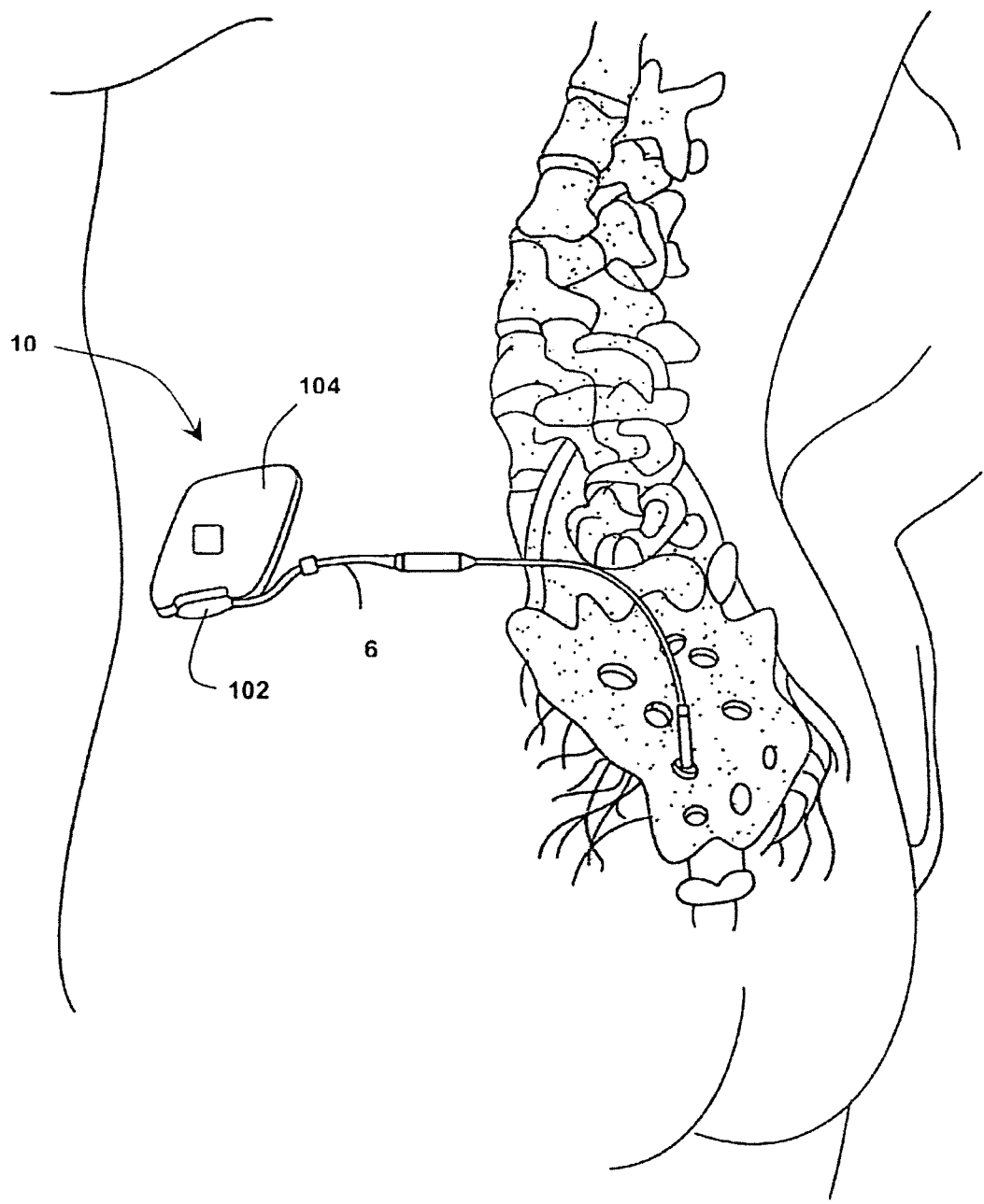
FIG. 2 is a system view of an exemplary implantable medical device for a neurological application.
Figure 3:
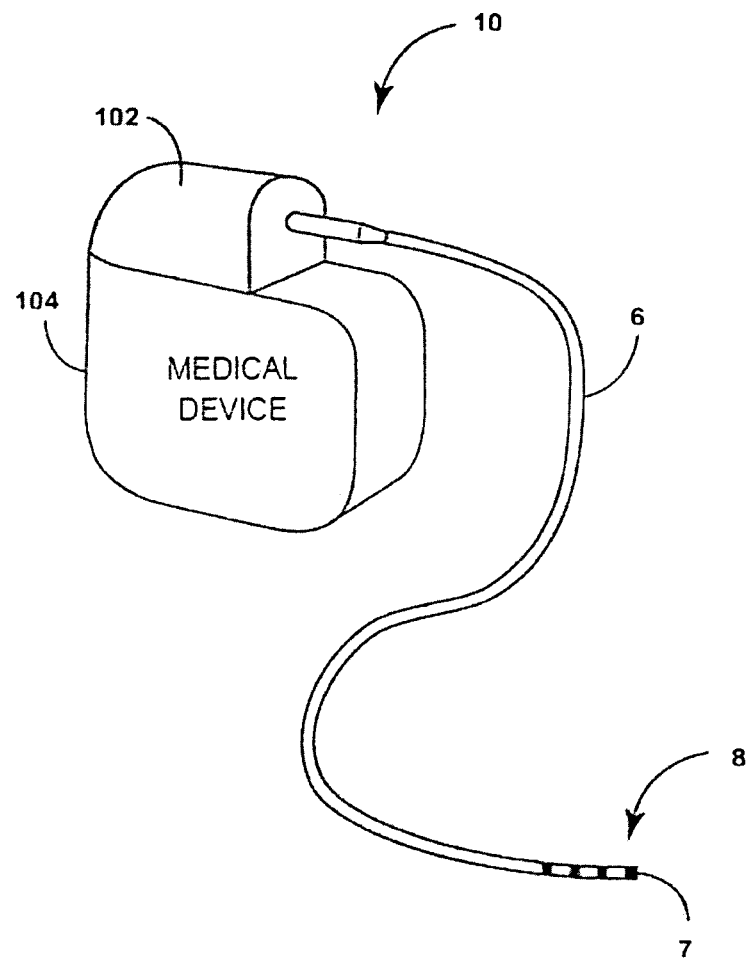
FIG. 3 is a schematic view of an exemplary implantable medical device.
Figure 4:
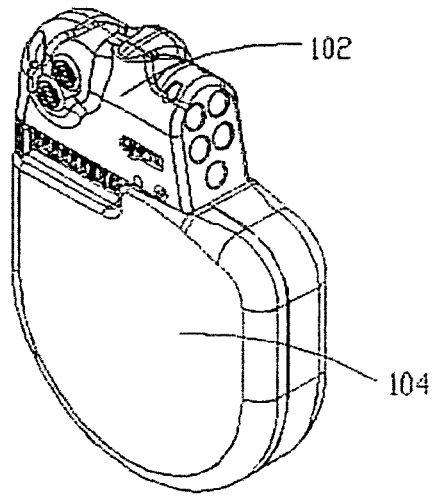
FIG. 4 is a perspective view of an exemplary implantable medical device (IMD).
Figure 5:
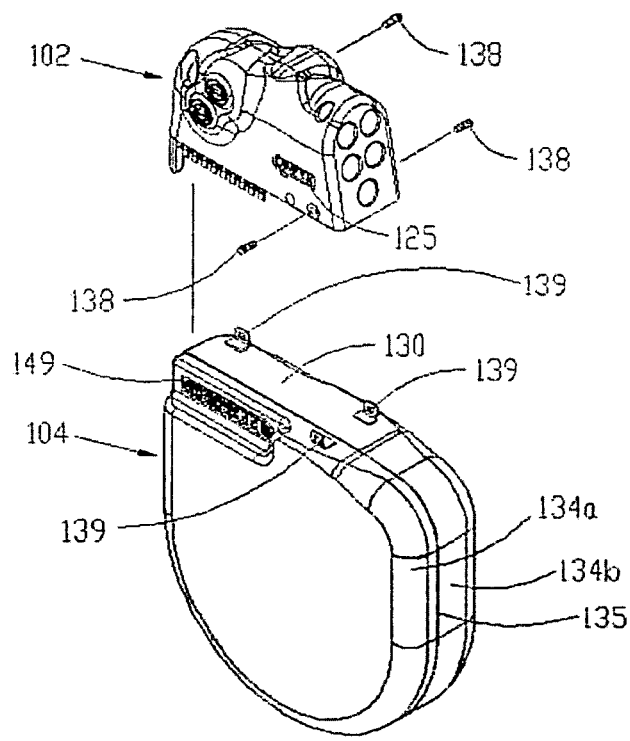
FIG. 5 depicts the IMD of FIG. 4 in which the connector is physically separated from the housing.

FIGS. 1-3 depict various exemplary implantable medical device systems 10, such that FIG. 1 depicts an implantable medical device system 10 used in a cardiac application and FIG. 2 depicts an implantable medical device system 10 used in a neurological application. Medical device systems 10 can include a housing 104 that encases an electronic module assembly (EMA) and a connector 102 (also referred to as a header) attached to the housing 104. The connector 102 can have an opening that may comply with an industry standard (e.g. industry standard (IS)-1, defibrillation (DF)-1, IS-4 etc.) that electrically couples various electronic components contained within the housing 104 of the IMD to a medical lead 6. A medical device system 10 and IMD may comprise any of a wide variety of medical devices that can optionally include one or more medical lead(s) 6 such as pacing and/or defibrillation leads and circuitry coupled to the medical lead(s) 6. An exemplary medical device system 10 may take the form of implantable medical devices (IMDs) such as an implantable cardiac pacemaker, an implantable cardioverter (ICD), an implantable defibrillator, an implantable loop recorder, an implantable cardiac pacemaker-cardioverter-defibrillator (PCD), a neurostimulator, a sensing lead (e.g. oxygen sensor, pressure sensor, chemical sensors etc.), a tissue or muscle stimulator and/or combinations thereof. Exemplary IMDs are commercially available as including the Medtronic CONCERTO™, SENSIA™, VIRTUOSO™, RESTORE™, RESTORE ULTRA™, sold by Medtronic, Inc. of Minnesota. Non-implantable medical devices or other types of devices may also utilize connectors such as external drug pumps, hearing aids and patient monitoring devices or other suitable devices. Medical device systems 10 may deliver, for example, pacing, cardioversion or defibrillation pulses to a patient via electrodes 8 disposed on distal end 7 of one or more lead(s) 6. Specifically, the lead 6 may position one or more electrodes 8 with respect to various locations so that medical device system 10 can deliver electrical stimuli to the appropriate locations.

Referring to FIGS. 4-9, connector 102 is electrically and mechanically connected to a housing 104. The housing 104 generally consists of two sides 134a and 134b that are seam welded 135 around or along a perimeter to form a hermetic seal between two sides 134a and 134b. The housing 104 protects the internal components of the IMD that, inter alia, includes an electronic module assembly (EMA). Exemplary internal components could be hybrid circuitry, battery, or other IMD components. One or more feedthroughs 149 are configured to conduct electrical signals including signals such as radio frequency signals through the housing wall while maintaining a hermetic environment within the housing 104.

The connector 102 is attached to a receiving area 130 of the housing 104. Attachment of the connector 102 to the housing 104 can be by any suitable means, for example, by the use of one or more straps 139 that accept corresponding pins 138 that are placed through corresponding holes within the connector 102. Optionally, attachment of the connector 102 to the housing 104 can be accomplished or assisted by the use of medical adhesive, such as a silicone based adhesive, placed between the connector 102 and the housing 104. Other suitable attachment means can also be used to couple connector 102 to the housing 104 such as laser welding, resistance spot welding, various fasteners, etc. Optionally, connector 102 may contain a radiopaque 125 for the purpose of device/model identification through X-ray imaging.

Figure 6:
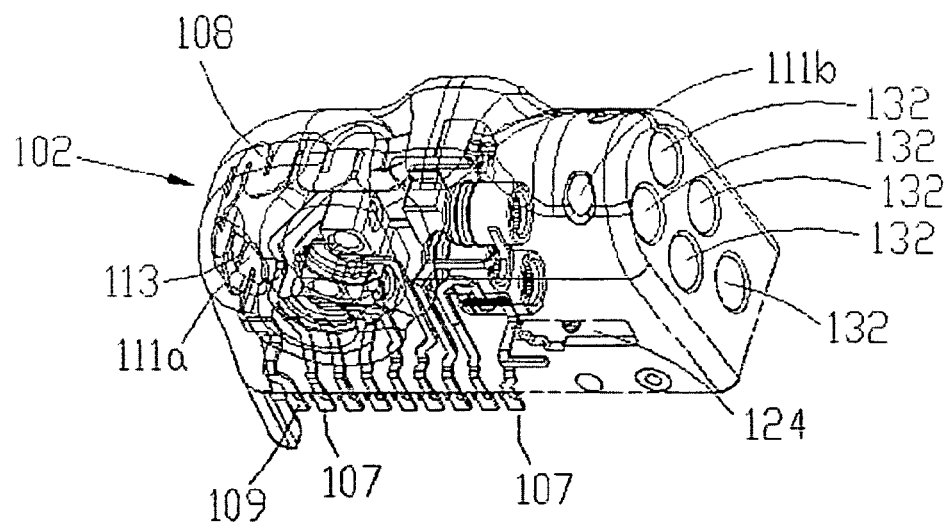
FIG. 6 is a perspective view of an exemplary connector with hardware components contained therein.

FIG. 6 is an exemplary connector 102 shown prior to attachment to the EMA. In one embodiment, connector 102 contains an antenna 108, for distance telemetry communication via radio frequency (RF) signals. In another embodiment, antenna 108 has an undulating serpentine design to increase the effective length of the antenna in order to improve telemetry performance. The connector 102, in one embodiment, has a front suture hole 111b and a back suture hole 111a that serve as a point of attachment to optionally suture the IMD to the tissue of the patient. Within the back suture hole 111a, clamping area 113 allows the subassembly and first component to be held in a fixed position during an overmolding operation. Preferably, in one embodiment, clamping area 113 is integral with the rear suture hole 111a. Clamping area 113 could be an element independent from the suture hole, or the clamping feature could exist on its own without the existence of any suture hole. The clamping area can be integrated into the outer profile of the connector 102. In still yet another embodiment, the clamping area could include a recessed area that is later filled with additional material as part of an additional operation.

A plurality of interconnect ribbons (ICRS) 107 protrude from the thermoplastic material at the bottom of the connector 102 including an ICR ribbon dedicated to the antenna 109. Each ICR ribbon connects to a feedthrough wire on the EMA to a setscrew block, multi beam contact (MBC), antenna, or other suitable component(s) contained within the connector 102. Optionally, a radiopaque cavity 124 may be present for receiving a radiopaque into the cavity 124 and can subsequently be covered by a medical adhesive such as NUSIL 2000™ commercially available from NuSil Technology LLC located in Carpinteria, Calif. The radiopaque could also be overmolded without using radiopaque cavity 124. Connector 102 optionally includes a set of apertures 132 or holes for receiving elongated medical leads.

Figure 7:
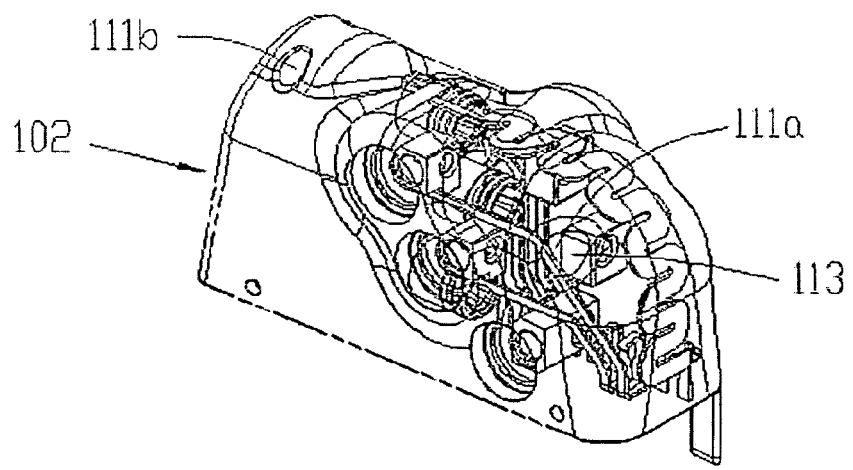
FIG. 7 is a perspective view of an opposite side of the connector depicted in FIG. 6.

FIG. 7 is a perspective view of the opposite side of the connector 102 shown in FIG. 6. The front and back suture holes 111b, 111a respectively, as well as the clamp area 113 are indicated in this view. The clamp area 113 from FIGS. 6 and 7 is generally symmetric to provide for opposed contact by each corresponding area of the mold and as will be explained in further detail later in the detailed description.

Figure 8:
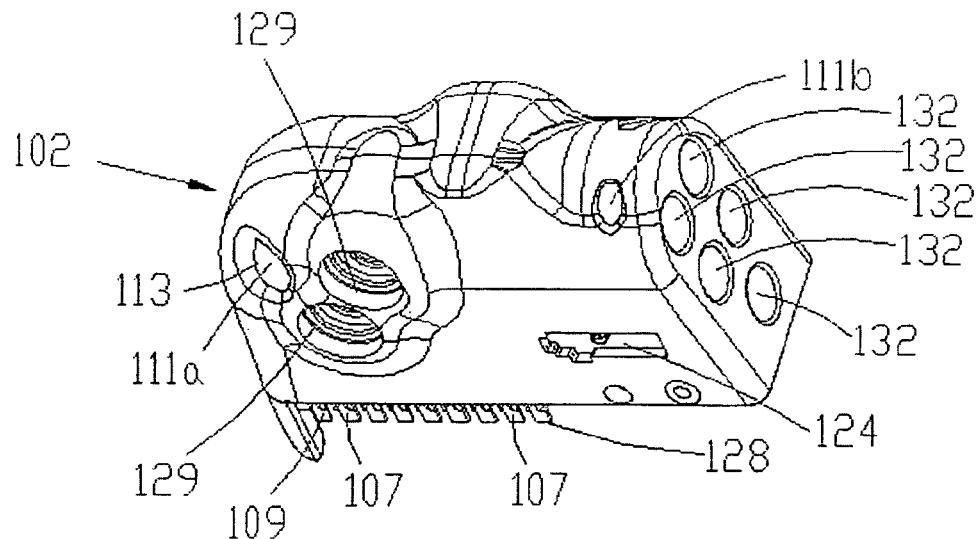
FIG. 8 is a perspective side view of the connector shown in FIG. 6 with the hardware components hidden to emphasize the final formed shape after overmolding or introducing a second shot of polymeric material over a first shot of polymeric material.

FIG. 8 is a similar perspective view of the connector 102 shown in FIG. 6 but with the hardware components hidden to emphasize a final form shape after overmold injection of a second polymer. Grommet cavities 129 for acceptance of grommets that provide electrical isolation and that allow a tool to penetrate therethrough to tighten setscrews and radiopaque cavity 124 may optionally be included on a connector 102. The overmold biocompatible thermoplastic material forms a layer of encapsulation over a significant portion of the hardware components. Exemplary thermoplastic materials include polyurethane such as Pellathane™ commercially available from Dow Incorporated located in Midland Mich., or Tecothane® commercially available from Noveon Incorporated. Other polyurethane materials are suitable for use in the present disclosure, as are other thermoplastic materials such as polysulfone. Polysulfone is commercially available from SOLVAY S. A. located in Brussels. If the connector 102 includes apertures or holes for the installation of lead 6 then the thermoplastic material is preferably constructed out of a substantially translucent polymer to allow for visual verification that an installed lead 6 is present. An opaque overmold polymer is also possible and would look similar to the embodiment as shown in FIG. 8 with emphasis on the final outer shape that encapsulates the hardware components. The opaque overmold polymer may be preferred for connector 102 that do not support the installation of leads.

Figure 9:
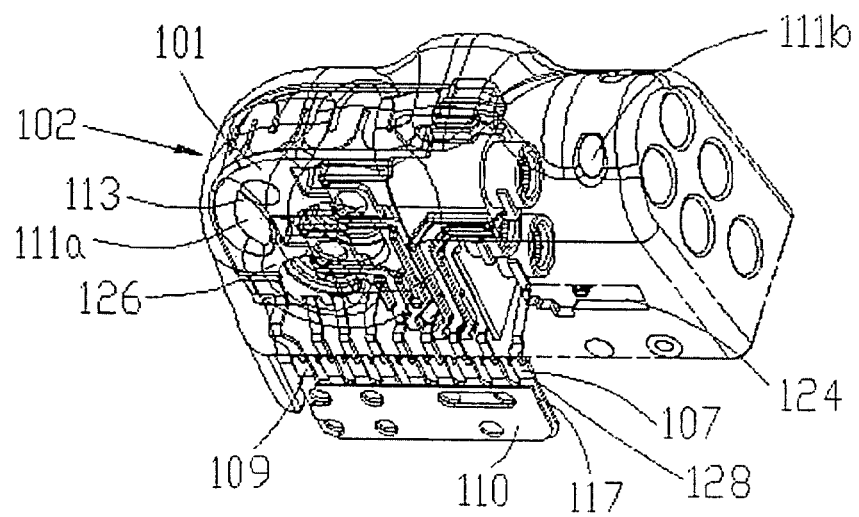
FIG. 9 is a perspective side view of the connector shown in FIG. 6 with hardware components attached to a first component of polymeric material.

FIG. 9 illustrates the same connector 102 shown in FIG. 6 and FIG. 8 but with the first component 101 (also referred to as a core portion or a polymer framework) made visible for the purpose of illustrating its positional relationship to the final overmolded shape. In one embodiment, the first component 101 is formed from a first shot of a polymeric material such as polyurethane, silicone or other suitable material. In one embodiment, a first shot comprises polymeric material that is inserted into a container of an injection molding machine and is introduced into the mold. In another embodiment, a first shot of a polymeric material is formed from injection molding of polymeric material over a hardware component. A weld plate 110 can optionally be used for manufacturing processing purposes. The ICR plate 117 is connected to the ICRs 107 and the antenna ICR 109 and serves the purpose of having a surface to attach the weld plate 110 that upon attachment serves to hold the ICRs in a fixed position relative to one another during the overmolding process. The weld plate 110 and the ICR plates 117 can be removed by a trimming operation later, prior to attachment of the connector 102 to the housing 104. The ICR trim point 128 is the location where the trimming occurs.

Figure 10:
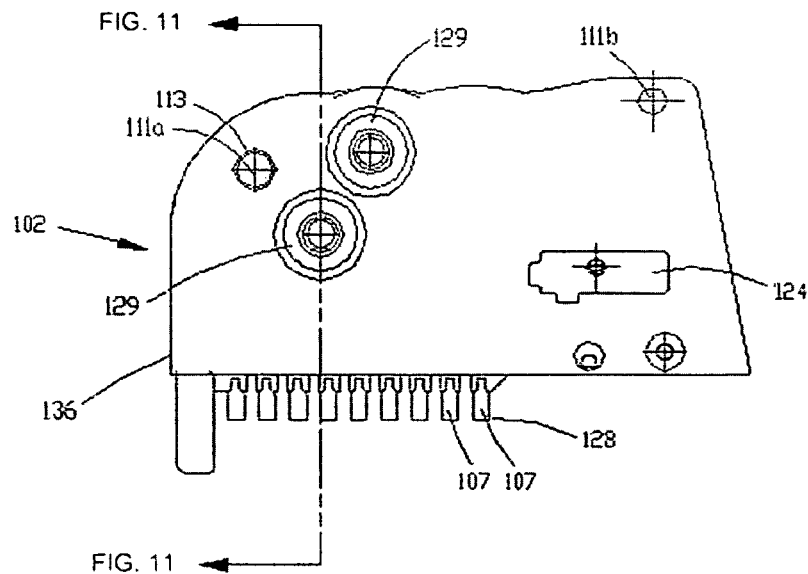
FIG. 10 is a side view of the exemplary connector introduced in FIG. 6.
Figure 11:
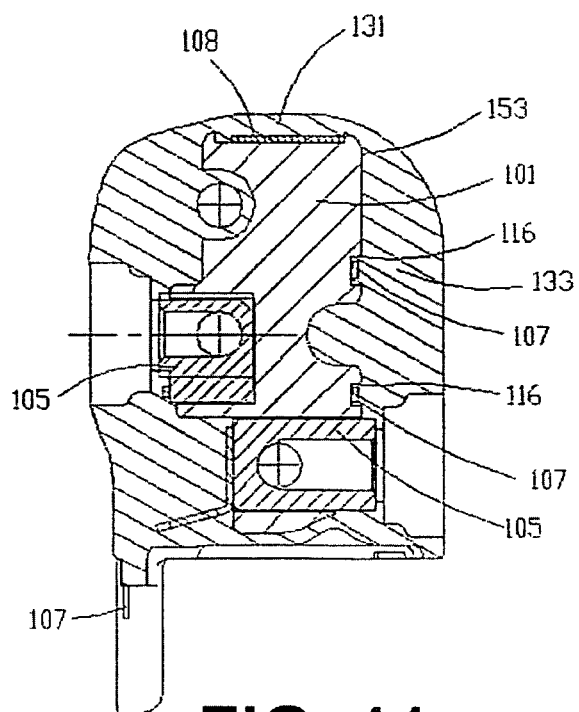
FIG. 11 depicts a cross-sectional view of the connector in FIG. 10, in which the position of the first component, antenna, and other hardware components within the connector are shown.

FIG. 10 depicts a side view of the exemplary connector 102 introduced in FIG. 6. FIG. 11 is a cross-sectional view of the section indicated in FIG. 10 through the lower grommet cavity 129. The sectioned view of FIG. 11 illustrates the position of the first component 101 within the overmold portion 133 (also referred to as a second component). The setscrew blocks 105 are installed into pockets within the first component 101 and the ICRs 107 are installed into channels 116 within the first component 101, both installations occur prior to overmolding the overmold portion 133. The antenna 108 can be installed into a dedicated channel on the first component 101 prior to being covered by overmold portion 133. The overmold portion 133 provides a dielectric 131 for the antenna. The gate location 136 is at the back of the connector 102 but could be in another location or a plurality of locations depending on the characteristics of the desired connector and the related mold design, which could differ substantially from this particular example.

Figure 12:
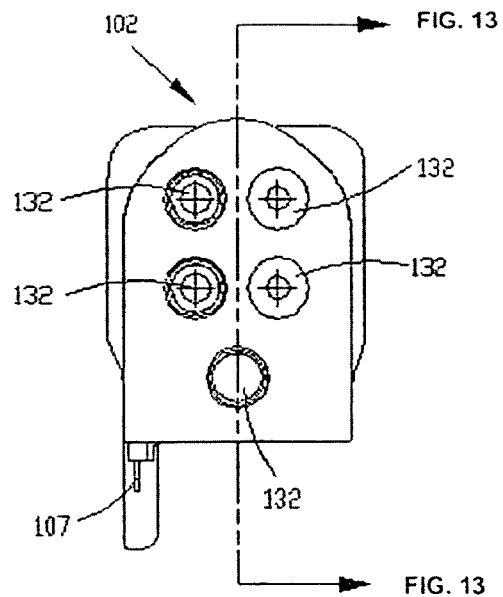
FIG. 12 depicts a front view of a connector with leadbore openings.

FIG. 12 depicts a front view of the connector 102 in FIG. 10 looking directly down the leadbore openings 132. If present, there can be various types of leadbore openings including for example openings that meet the IS-1 (ISO 5841-3) or DF-1 (ISO 11318) standards. The present invention is not limited to connectors that have leadbore openings. For example a connector 102 may have other hardware component(s) contained within it such as an electrode, sensor, or antenna and therefore the presence of leadbore openings is not a required aspect of the connector 102. The Reveal™ Plus insertable loop recorder, a subcutaneous diagnostic and monitoring device, produced and marketed by Medtronic Inc., exemplifies an IMD that has a connector that contains a hardware component, an electrode, but does not have openings for the purpose of connecting leads to the device. Devices such as the Reveal™ Plus and other IMDs with connector 102 may find the present disclosure useful for the purpose of installing one or more hardware components.

Figure 13:
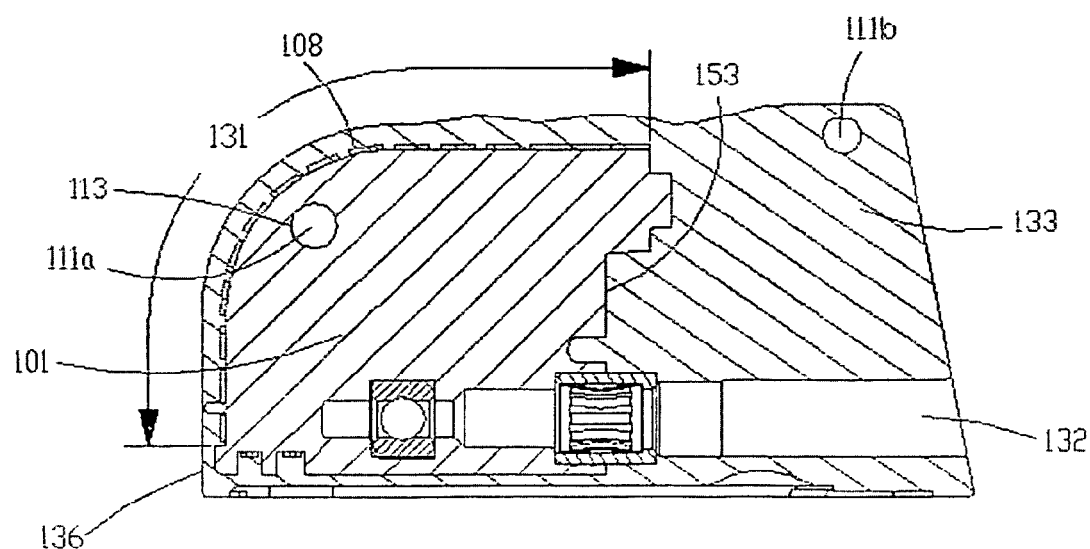
FIG. 13 is a cross-sectional view of the section depicted in FIG. 12.

FIG. 13 depicts a cross-sectional view of the section indicated in FIG. 12 which illustrates the position of the first component 101 within the overmold portion 133. This section also illustrates that the antenna 108 is adjacent the first component 101 which it is attached thereto prior to the overmolding operation and as will be explained in greater detail below. This particular section view also highlights the position of the gate location 136 in this particular embodiment relative to the first component 101 as well as showing the coverage of the antenna 108 with overmold portion 133 which provides a dielectric over the antenna 131. The thickness of the dielectric 131 can be adjusted to provide optimal antenna telemetry performance and consistent dielectric thickness between different manufactured devices. Additionally, the position of the antenna 108 within the connector 102 material relative to other metal components contained within the connector 102 such as ICRs, connector blocks, radiopaques, or other metal components should be reasonably consistent given that there can be RF coupling between the antenna and such components during RF transmission or reception. The present disclosure, by allowing the first component 101 to be rigidly held in an opposed manner by the mold during overmolding, allows for improved consistency of the thickness of the dielectric ray dome as well as improved positional control of the antenna within the connector 102. Likewise, the present disclosure provides for improved positional control of other hardware components that are to be installed into a connector 102.

Referring back to FIG. 11 and FIG. 13, a crisp line of distinction, referred to as a knit line, or interface area 153 depicted between the first component 101 and the overmold portion 133. However, upon overmolding, and if a thermoplastic polymer is injected as the overmold material, the interface area between the first component 101 and overmold portion 133 can be a blurry interface area. For example, at the interface area melting can occur at the edges of the first component 101 in the interface area 153 between the first component 101 and the overmold polymer as the heated overmold plastic flows over it causing it to mix with the overmold portion 133. The amount of melting and mixing between the two is highly dependant on the part design as well as mold design, particularly how and where the mold for overmolding is gated and the location of the gate or gates.

Figure 14:
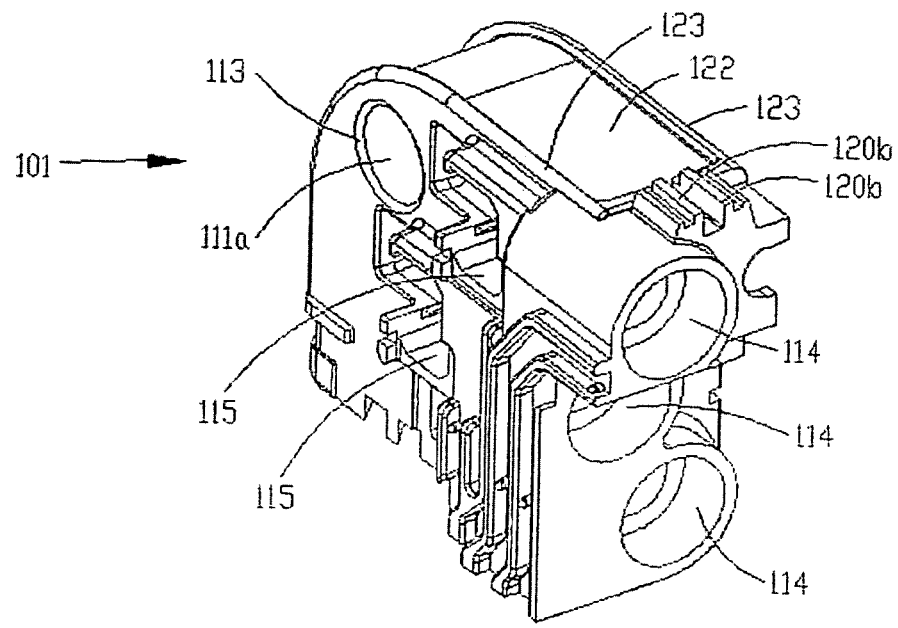
FIG. 14 is a perspective view of a first component, which is a component of the exemplary connector of FIG. 6.
Figure 15:
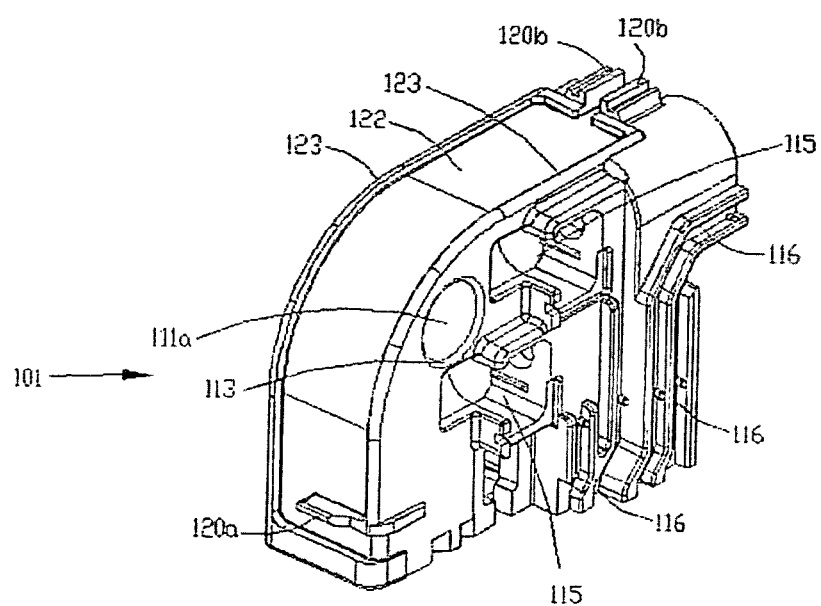
FIG. 15 is an additional perspective view of the first component in FIG. 14.
Figure 19:
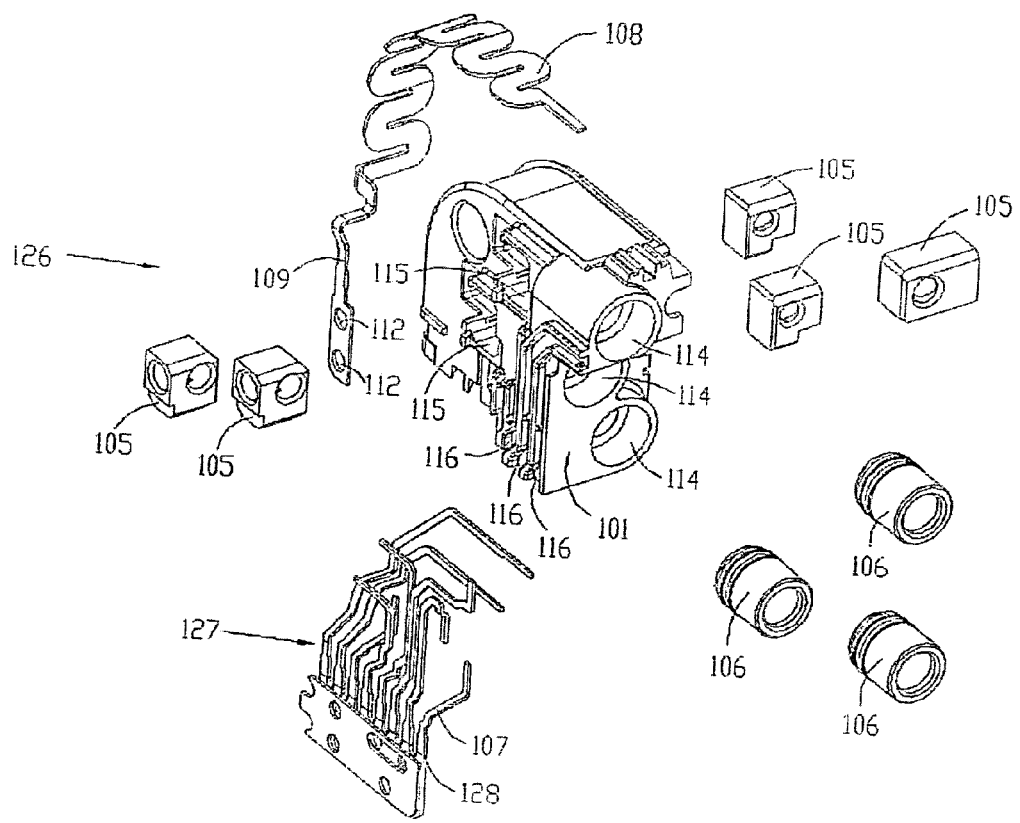
FIG. 19 depicts an exploded view of the subassembly in FIG. 18.

Referring now to FIGS. 14-15, details of a first component 101 are depicted. This is the same first component 101 introduced in the exemplary connector 102 of FIG. 9. At the top and back of the first component 101, there is a channel 122 for the purpose of accepting or receiving an antenna hardware component. The channel 122 is defined by a ridge 123 on either side of the channel 122 for the purpose of constraining the antenna hardware component upon coupling or installation of the antenna adjacent the first component 101. At the top of the first component 101 and at the end of the channel 122 there is a pair of front sacrificial staking features 120b that are melted so as to cover and hold the front of the antenna upon coupling of the antenna adjacent the channel 122 surface, as shown FIG. 16 and the accompanying text but with exception of the melting of the staking features 120b, that are not shown melted in FIG. 16.

The first component 101 has a specific clamping area 113 that enables the first component 101 to be held by the mold upon closing of the mold. While being held, an overmold operation where a second shot or layer of thermoplastic material is introduced to the mold over at least a portion of the first component. Preferably, the clamping area 113 is an integral feature with the back suture hole 111a. However, the clamping area 113 need not be integrated with the rear suture hole 111a as a requirement for having a clamping area. In fact, the suture hole is considered an optional feature and there are other designs for overmolded connector 101 for various other types of IMDs that do not have suture holes and nevertheless would be able to make use of the inventive aspects of the clamping area 113.

First component 101 can be configured to hold or support hardware components including MBC (multi-beam contact) receptacles 114 or receptacles setscrew blocks 115. The MBC 114 are referred to herein generically as MBC (multi-beam contact), the MBC 114, area shown as a generic cylindrical assembly that houses the multi-beam contacts themselves. The respective hardware components can be installed into the receptacle type openings. Also, channels 116 can be configured to receive and/or hold ICRs.

The first component 101, in one embodiment, is formed of a thermoplastic material that is the same material as that of the overmold portion 133. Using the same thermoplastic material for both the first component 101 and overmold portion 133 provides the same melting points, thereby promoting good adhesion between the materials upon overmolding. The materials for the first component 101 and overmold portion 133 may be different and allows for compatible melt temperatures if the adhesion between the parts once overmolded is adequate for their intended use. Intended use may vary greatly among different connector 102, for example if the connector 102 contains components that supply high voltage therapy then the connector 102 design may have different design requirements versus connector 102 that houses a component that only sees low voltage. There may also be connector 102 designs where it is desirable to have the first component 102 and overmold materials be different from each other to achieve different performance characteristics for the respective areas of the finished connector 102. The construction method for the first component 101 is preferably injection molding, but could also be a machining process or a combination of a molding process and a machining process.

Coupling, or installation, of hardware components to the first component 101 is shown in FIGS. 16-19. A subassembly 126 is formed by installing hardware components adjacent to the first component 101. The setscrew blocks 105 are installed into setscrew block receptacles 115, that are called out in the exploded view, and likewise the MBC 106 are installed into MBC receptacles 114. In some embodiments, the setscrew blocks 105 and MBC 106 may be oversized relative to their corresponding receptacle in the first component 101 such that a press-fit exists upon installation of the component. In one embodiment, the press-fit acts to hold the component to the first component 101.

The ICR 107 can be installed into channels 116 and thereby coupled with the first component 101. Preferably, the channels are sized in localized areas so as to create a "press fit" between the channel 116 of the first component 101 and the ICR 107 upon installation of the ICR into the channel 116. The ICR can comprise niobium, titanium, stainless steel, or other conductive material. The ICRs 107 are attached to their corresponding set screw block 105 or MBC 106, typically by a welding, brazing, or soldering operation.

Referring now to FIG. 17. optionally, the ICR 107 can be grouped with other ICRs, through the use of an ICR plate 117. Grouping a set of ICRs together can reduce the number of components to handle as well as speed the process of installing the ICRs 107 to the channels 116 of the first component 101. The ICR plate is a manufacturing aid that can be removed at a later operation. The grouping of ICR 107 into a single ICR plate 117 can be determined by ICR that have like characteristics, for example ICR that are installed to the same side of the first component 101. In the case of the lone antenna ICR 109, or another single ICR, the ICR plate can represent a single ICR. Optionally, separate ICR plates 117 can be joined together by attachment to a single weld plate 110. The weld plate 110 binds the ICR plates 117 together for ease of installation to and alignment with the mold. Again optionally, the ICR plates 117 have position holes 112 that correlate to weld plate holes 112, using these holes pins can be inserted through the holes in order to force alignment between the ICR plates 117 and the weld plate 110. Held in this manner, the weld plate 110 can be attached to the ICR plates 117 by opposed electrode resistance spot welding or by any other suitable joining process. At a later operation, after the overmolding of the subassembly 126, the weld plate 110 and ICR plates 117 can be removed by cutting at the ICR trim point 128.

The antenna 108 can be constructed out of any suitable metal with acceptable biocompatibility and RF performance properties, the antenna in the preferred embodiment being constructed out of Titanium. The antenna 108 is coupled to or installed into a dedicated channel 122 on the first component 101 so that the antenna 108 is adjacent the first component 101. Sacrificial staking features at the front 120b and back 120a are designed to hold the antenna 108 adjacent to the first component 101 upon a staking operation. The dual front staking features 120b are positioned to either side of the antenna tip and act to hold the antenna 108 once they have been staked and at which point they become pressed onto the tip of the antenna 108 thereby covering it with first component material and holding it. Upon installation of the antenna 108 within the channel 122 of the first component 101, the single back staking feature 120a becomes positioned at the inside of the last "U" portion of the antenna 108, or where the serpentine portion of the antenna reverses. Upon staking of feature 120a, the polymer of the feature is compressed and expands out over the antenna 108 thereby holding the antenna 108 adjacent to the bottom of the channel 122 of the first component 101. The method of staking the features 120a and 120b is preferably ultrasonic staking but could also be heat staking or any other suitable method to melt and reposition the polymer that defines staking features 120a and 120b so that they are pressed onto and thereby hold the antenna 108 to the first component 101. As an alternative to the method of staking, or in addition to it, the antenna width could be oversized relative to the width between the ridges 123 so that a "press fit" is created to hold the antenna in a fixed position to the first component 101.

Note that other methods of coupling the setscrew blocks 105, MBC 106, ICR 107, antenna 108, or other hardware component to the first component 101 are possible and would be compatible with the present disclosure in so far as the hardware component is sufficiently held to the first component 101 during the overmolding operation so that there is no undesirable movement of the hardware component relative the first component 101. Any movement between first component 101 and the hardware component correspondingly impacts the position of component within the finished connector 102. The overmolding operation subjects the subassembly of first component 101 with hardware 126 to considerable turbulence and will be described in greater detail later in the description. However, it is the ability to withstand the overmold operation with proper positioning of the hardware component that defines if the hardware component is adequately attached to the first component 101.

Figure 20:
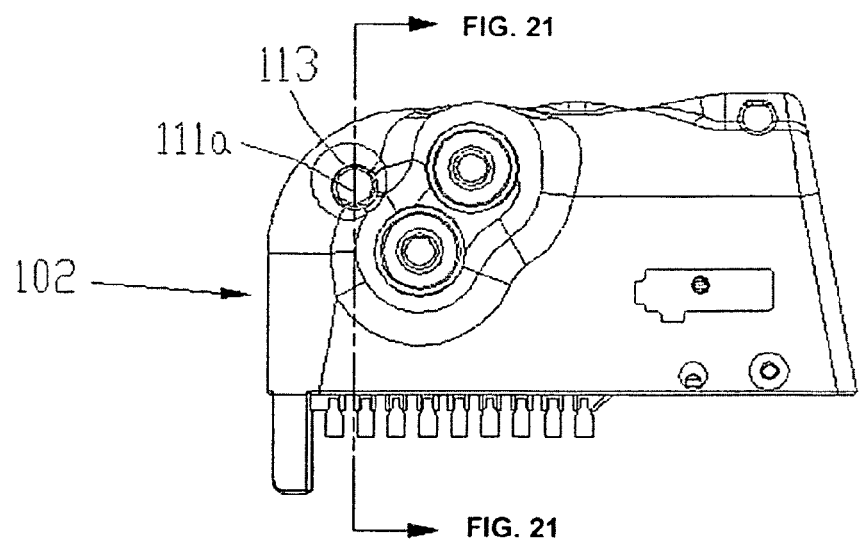
FIG. 20 depicts a side view of an exemplary connector with the hardware and first component hidden.
Figure 21:
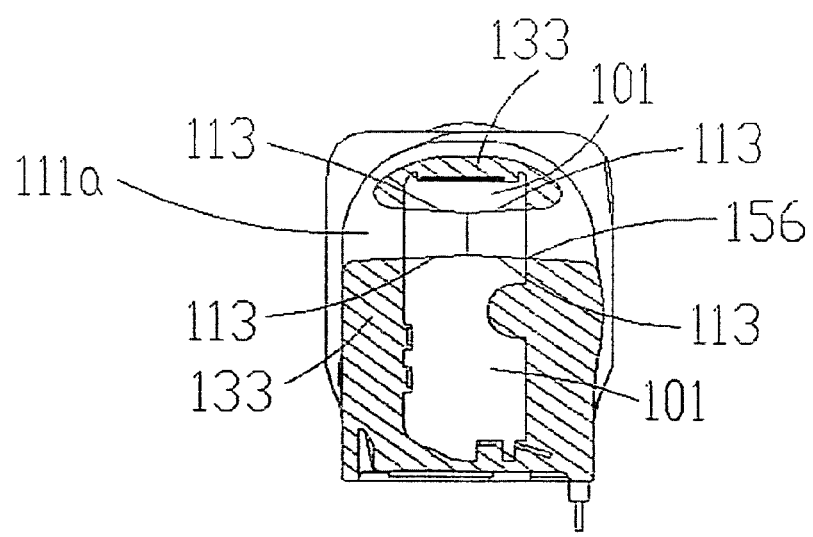
FIG. 21 depicts a cross-sectional view of the section indicated in FIG. 20.

Referring now to FIGS. 20-21, depict a side view and a cross-sectional view of the exemplary connector 102 of FIG. 6 and constructed using the example first component 101 and subassembly from FIGS. 14-19. FIG. 21 depicts the section indicated in FIG. 20 that slices through the center of the rear suture hole 111a and first component 101 clamping area 113. The first component 101 is encapsulated by overmold material 133 with the exception of the clamp area 113 where the first component 101 is exposed and abuts the overmold polymer. The exposed area of the first component 101 in the clamping area 113 allows for direct contact with an area of the overmold mold tooling and allows the mold tooling hold location 113 from opposing sides during injection of an overmolding thermoplastic material. By holding the first component 101 in this manner the subassembly 126, comprising first component 101 with a hardware component, is held in a fixed position during high pressure injection of the overmold polymer. Consequently, first component 101 and adjacent hardware components are securely held in a stationary position.

Upon inspection of the finished connector in the area where the first-shot abuts the overmold polymer, adjacent the clamp area 113, there will be apparent a knit line 156. The knit line 156 can be determined upon visual microscope inspection or cross-sectioning of the connector 102. A knit line 156 delineates an interface, formed of a set of points or a planar surface, between the first and the second components 101, 133. The knit line 156 is created after a first shot of polymeric material forms into the first component 101 followed by a second shot of polymeric material introduced over the first component 101. The second shot of polymeric material forms the second component or overmold portion 133. The knit line 156 directly abuts itself between the first and the second components 101, 133. A knit line 156 can also occur where different polymers or different shots abut one another.

Figure 22:
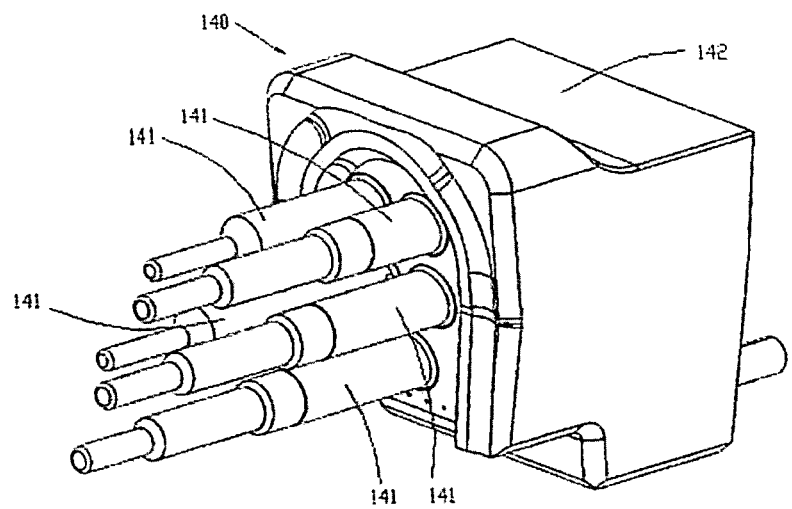
FIG. 22 depicts a removable component that may be an integral component of an injection mold used in an overmolding operation.
Figure 23:
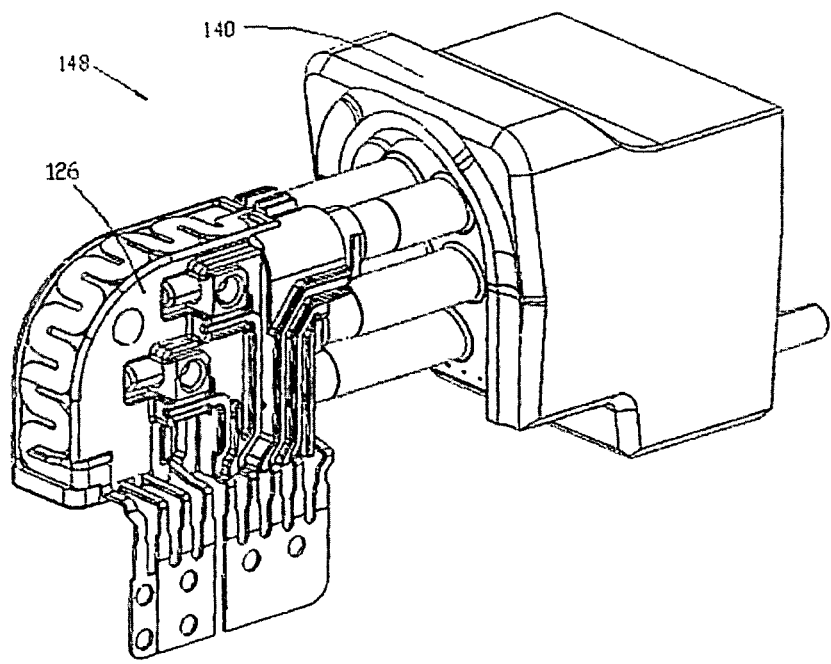
FIG. 23 shows the removable component of FIG. 22 with the subassembly of FIG. 16 installed thereto.

Referring now to FIGS. 22-23 an exemplary subassembly 126, formed of a first component 101 with a hardware component, can be prepared for introduction into a mold used for overmolding. FIG. 22 depicts a leadbore core pick-out 140 which is simply a removable section of the mold 143 of FIG. 24. The leadbore pick-out 140 allows for subassembly 126 to be introduced into a mold that is then used for performing an overmolding operation. The leadbore pick-out 140 has a main body 142 and leadbore core pin 141 features that protrude therefrom. The core pin 141 may be a separate piece of steel that is "press fit" or otherwise installed into the main body 142. Each of the core pin 141 is designed with a profile to engage in a "slip" or "press fit" with the corresponding shape of the openings in the first component 101 of the subassembly 126 and provides the inverse opening that will be created in the finished connector 102 upon introduction of an overmold polymer during the overmolding operation.

FIG. 23 shows the pick-out of FIG. 22 with the subassembly 126 introduced in FIG. 16 attached thereto, creating a leadbore core pin pick-out assembly 148. The leadbore core pin pick-out assembly 148 is used for loading the subassembly 126 into the mold and allows for controlled positioning of subassembly 126 with the mold. Upon installation of the subassembly 126, the created leadbore core pick-oult assembly 148 can then be installed into a mold cavity that will rigidly hold the leadbore core pick-out 140 and abut various adjacent sides of the mold as will be shown in the description of later figures.

The leadbore core pin pick-out assembly 148 is an optional component of the mold, used as one method to introduce the subassembly 126 into the mold. The use of a pick-out is not required to enable the invention and it is foreseeable that the invention may be practiced without such a feature and instead relying solely on the inventive clamping features on the first component 101 to hold the subassembly 126 within the mold. Furthermore, not all connectors 102 provide apertures for the installation of lead 6 and in such instances the use of a pick-out that engages the leadbore openings would not be applicable, although such a connector 126 may nonetheless be overmolded.

Figure 24:
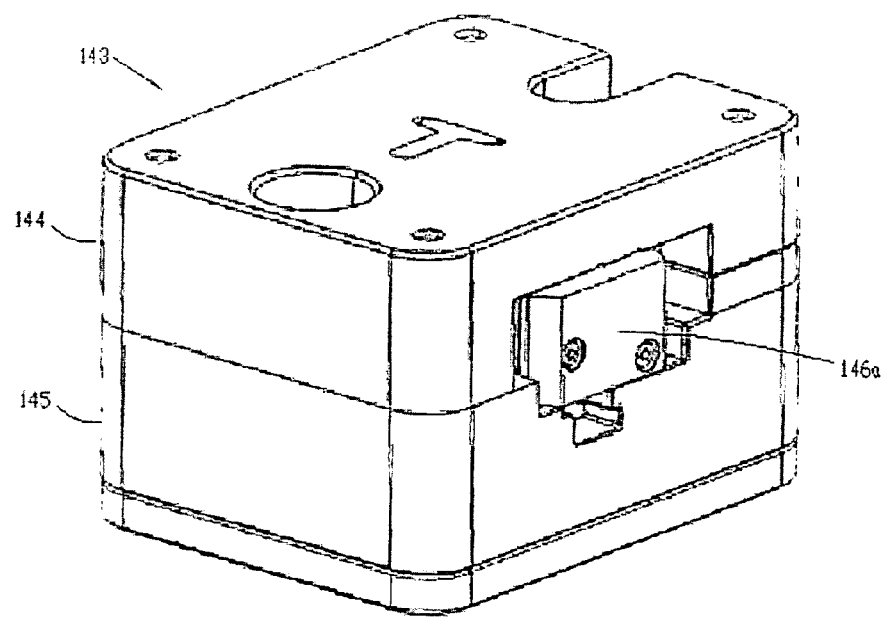
FIG. 24 shows an exemplary injection mold for applying an overmold polymer.
Figure 25:
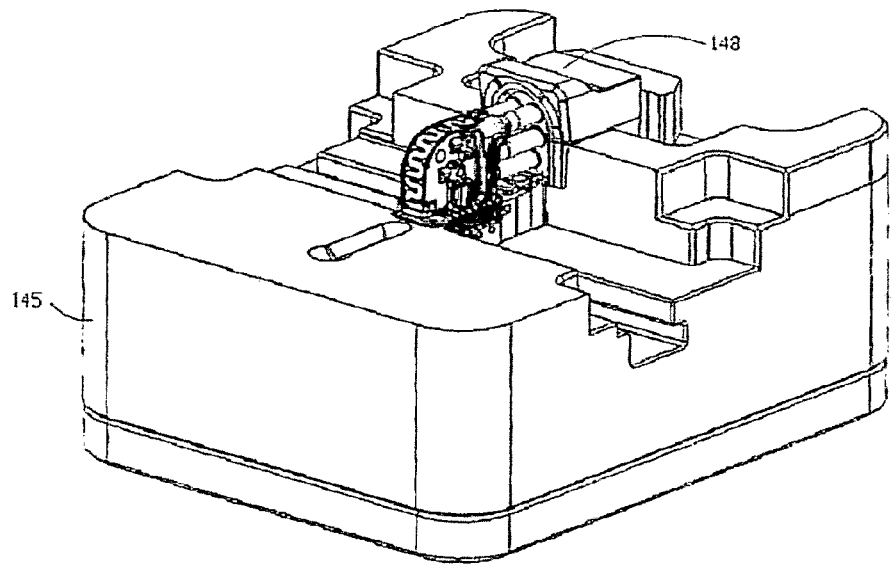
FIG. 25 shows the injection mold of FIG. 24 with top and side pulls removed.
Figure 26:
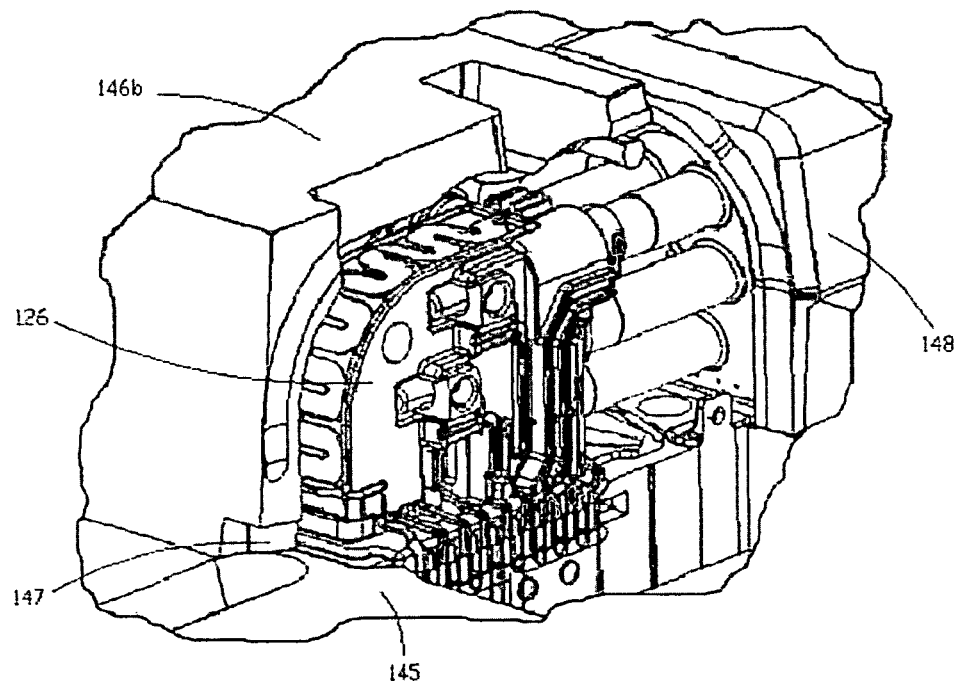
FIG. 26 is a cut-away view of the injection mold of FIG. 24 with the removable component, left side pull, and subassembly shown but with the molds top and right side hidden.

Referring now to FIGS. 24-26, an exemplary mold is depicted for performing the overmolding operation. FIG. 24 depicts a perspective view of an injection mold 143 that is used for an overmolding operation where thermoplastic material is introduced over the subassembly 126 of first component 101 with adjacent hardware component(s). The mold 143 has a top section 144 (a first side) and a bottom section 145 (a second side). The mold 143 can also have side pulls on either side, with only the right side pull 146a visible and the left side pull 146b not shown in this view but that is opposite the right side pull 146a.

FIG. 25 depicts the mold of FIG. 24 but with the top 144 and side pulls 146a and 146b removed. With these components removed the position of the leadbore core pin pick-out assembly 148 that is contained within the mold is illustrated. With the mold an open position, with the top 144 positioned away from the bottom 145 and the side pulls 146 pulled away from each other, the leadbore core pin pick-out is placed into the bottom side of the mold 145. Using this technique, the leadbore core pin pick-out assembly can be installed into the mold and afterwards the mold can be closed for allowing for injection of overmold polymer, which will be described below in greater detail.

FIG. 26 depicts a cut-away view of the mold of FIG. 24. The subassembly 126 of the first component 101 with hardware 126 is shown within the mold. The right's side pull 146a as well as the top portion 144 of the mold are removed from FIG. 26 but the bottom of the mold 145 and the left side pull of the mold 146b remain visible for the purpose of concept illustration as to the position of the subassembly within the mold. The gate location 147 provides an opening where molten polymer is injected into the mold until the cavity is full. In this example there is single gate opening. In other embodiments, it is feasible to have multiple gates, depending on the shape of the structure to be molded and/or thicknesses. The gate location 147 positioned at the lower back of the connector 102 based on the following rational in this example embodiment. First, the location of the gate is influenced by cosmetic aspects of the part being molded. In the case of a connector 102, it is desirable to have the gate location in an area where it does not irritate a patient's anatomy. The position at the lower back of the connector 102 is in a generally flat area relative to the overall IMD profile and shape. Second, having the gate location opposite the pick-out allows the high pressure force of the molten plastic upon introduction to the mold cavity to be applied to the subassembly 126 of first component 101 with hardware 126 in a direction that applies force towards the leadbore core pin pick-out assembly 148. This acts to help ensure that the subassembly 126 is fully seated on the pick-out assembly 148 as the subassembly 126 is over molded.

Figure 27:
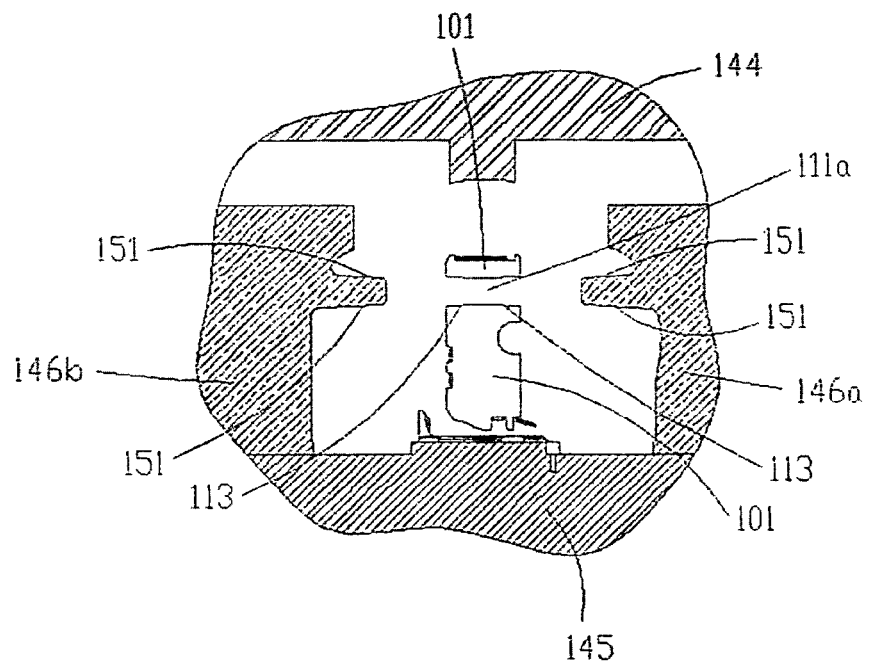
FIG. 27 is a cross-section of the subassembly through the clamping location of the first component within the mold of FIG. 24 with the top and side pulls of the mold in an open position.
Figure 28:
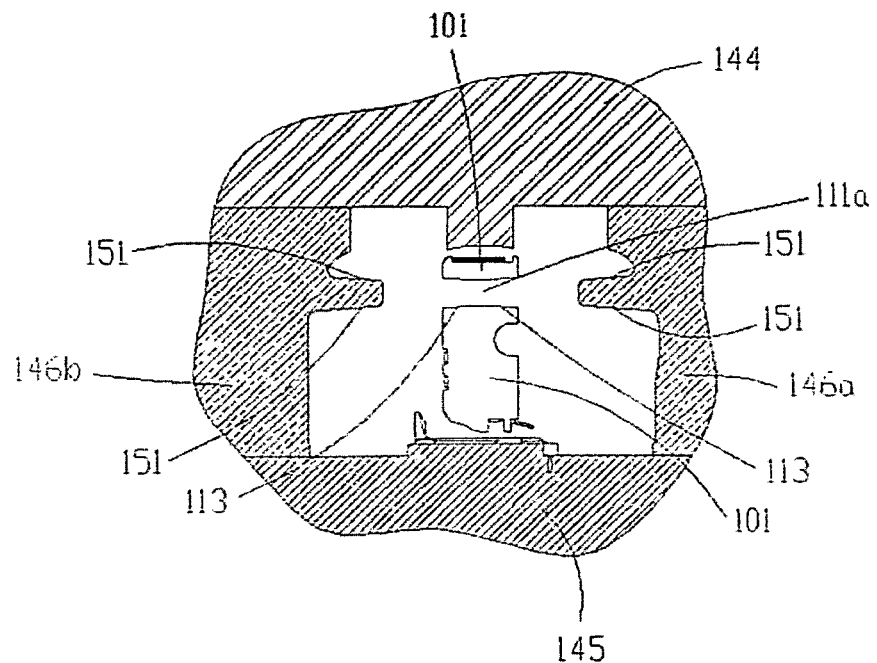
FIG. 28 is a cross-section similar to that shown in FIG. 27, but with the top of the mold in a closed position.
Figure 29:
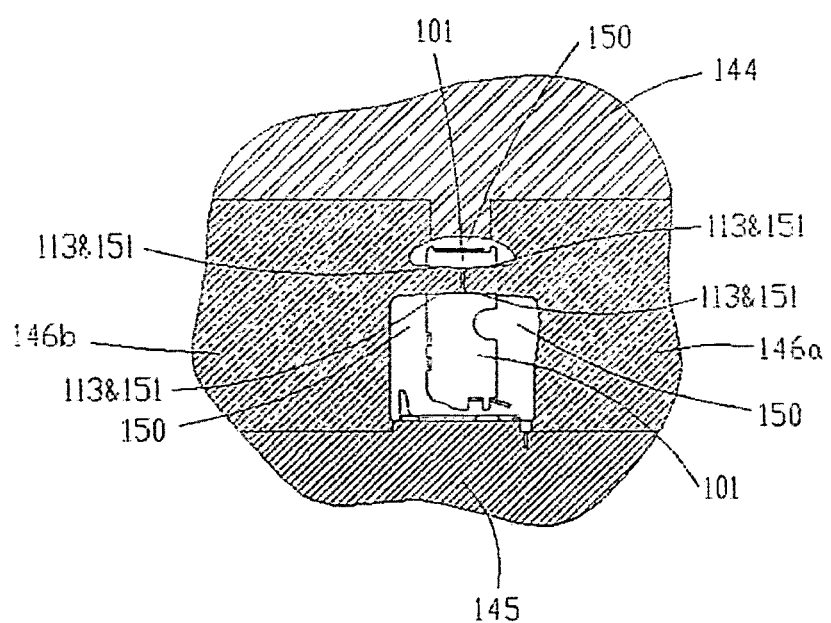
FIG. 29 is a cross-section similar to that shown in FIG. 28, but with the side pulls of the mold in a closed position and the other parts of the mold fully closed.

Now referring to FIGS. 27-29, an exemplary sequence of operations of the mold is introduced in FIG. 24. The view shown in these figures is a cross-section view through the same location as that of FIG. 21 sectioned through the clamping area 113 of the first component 101. The sides of the mold 146a and 146b can each be constructed out of a single piece of material or can be constructed out of multiple pieces of material.

In FIG. 27, the mold is shown in a fully open position as it would conceptually appear during placement of the optional leadbore core pin pick-out assembly 148 into the mold. In the open position, the top of the mold 144 is in a raised position and the respective side pulls 146a and 146b are in an open position that is moved away from each other and the first component 101. Not shown in this view, the first component 101 is held suspended by the leadbore core pin pick-out 140.

In the open position shown, the holding or clamping areas of the mold 151 do not yet contact the clamping areas 113 of the first component 101.

In FIG. 28, the mold is shown in a partially open position with the top of the mold 144 now in a closed position and that is the next sequence in the mold closing from that described in FIG. 27. The respective side pulls 146*a* and 146*b* are still in an open position, and therefore the holding areas of the mold 151 do not yet contact the clamping areas 113 of the first component 101.

In FIG. 29 the mold is shown in a fully closed position with both the top of the mold 144 and the sides of the mold 146*a* and 146*b* in a closed position. In this closed position the holding area of the mold 151 on both the right side of the mold 146*a* and the left side of the mold 146*b* area adjacent the points of contact with the clamping area 113 on each respective side of the first component 101. Through these opposing points of contact, the first component 101 and hardware components fixed thereto are held by the opposing sides of the mold 146*b* and 146*a*.

The amount of clamping force that is generated by the opposing points that interlock with the first component 101 is adjustable by sizing the width of the first-shot between the clamping areas 113. For example, if the width of the first-shot in this area is enlarged then there will be a corresponding increase in the clamping force provided by the two opposing sides of the mold 151. In another embodiment, only one of the two opposing sides of the mold applies clamping force wherein the other side remains stationary. It is preferred that there is some amount of clamping force. However, the fit can also be line-to-line and thus not generate any clamping force yet still provide adjacent physical constraint by the mold for the first component 101 during overmolding.

In an alternative embodiment to that shown in FIGS. 27-29, for example the molding of a connector 102 with no leadbores, the first component 101 could be placed on one side of the clamping area and could be held there by gravity (if the mold were tilted 90 degrees), or by a "press-fit" or "slip-fit" of the first-shot clamping area with one side of the mold holding area. Upon fully closing of the mold the first-shot would become fully clamped by the mold. This method of holding the first-shot would be in lieu of the method described above associated with where the first-shot is held in the mold by the leadbore core pin pick-out.

Figure 30:
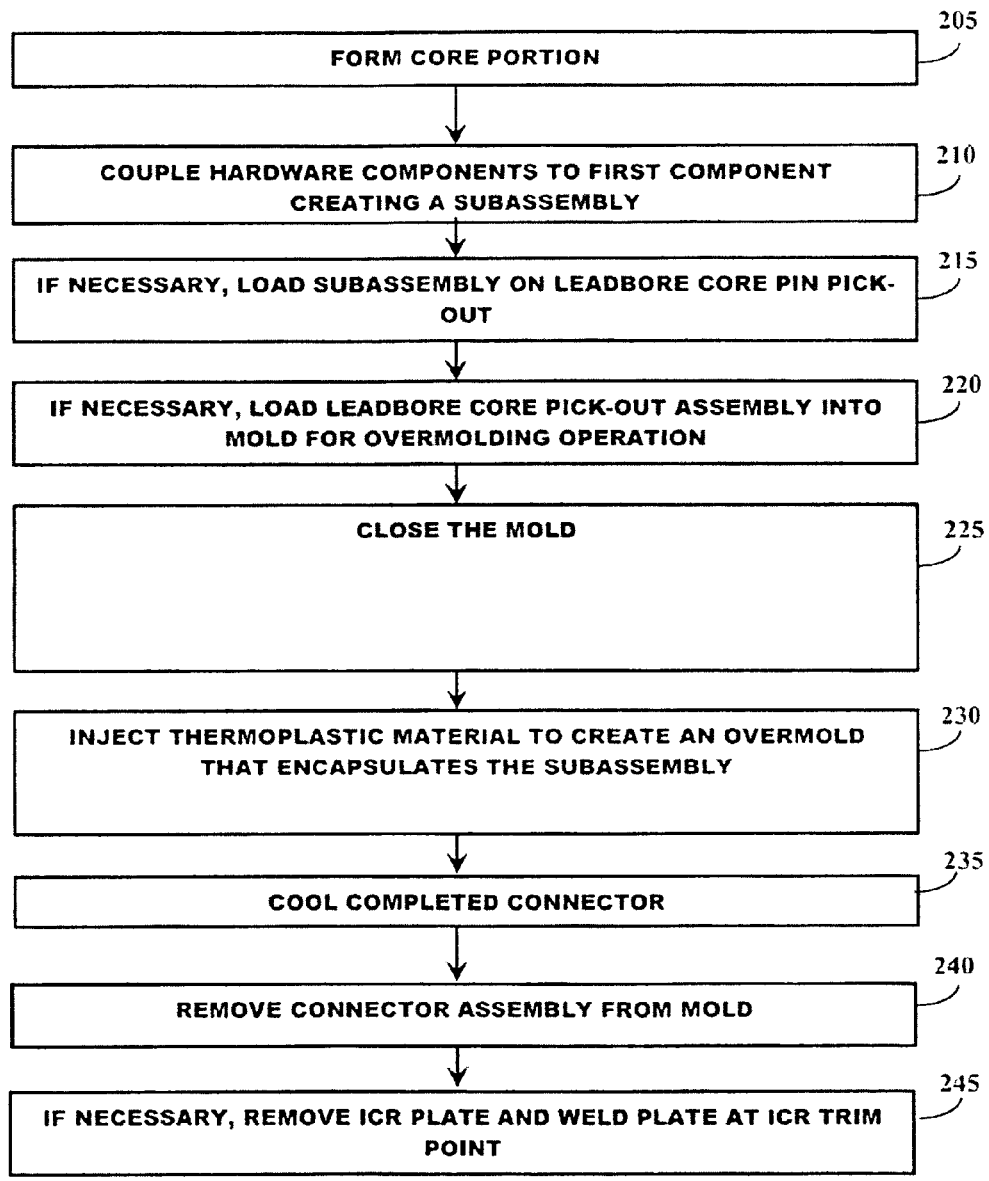
FIG. 30 is a flow diagram that depicts operations to form an exemplary connector.

FIG. 30 is a flow diagram highlighting the operations utilized to make an exemplary connector 102. Although for discussion purposes the associated description involves the first-shot to form first component 101 of FIG. 14, the subassembly 126 in FIG. 16, and the connector 102 of FIG. 8, it will be understood that the described process is equally applicable to the production of other connector 102 with fewer hardware components or hardware components that are altogether different from those of the first-shot 101 in FIG. 14, the subassembly 126 in FIG. 16 and connector 102 of FIG. 9. In the starting operation 205, the first-shot is formed out of a thermoplastic material. In one embodiment, a first shot is formed by an injection molding process or by a fabrication process such as machining, or the construction could be a combination of such methods. In operation 210, the hardware component or components are coupled to the first component 101. The hardware component(s) can be coupled by installing it adjacent the first component 101. The hardware component may be a component such as a setscrew block, antenna, MBC, ICR, radiopaque, radio frequency identification (RFID), sensor, such as a sensor to sense a physiological parameter, or could any other component where it is desired to position the component within the connector 102 such that the component becomes at least partially encapsulated within the connector 102 via an overmolding operation. This operation can include coupling or affixing the hardware components adjacent the first-shot which can be accomplished by a staking method using heat or ultrasonic energy to cover a portion of the component with the first-shots own thermoplastic material or another material. This operation may also include placing the hardware component into a mating structure on the first component 101 such as openings for the setscrew blocks or channels for ribbon-like components. Other suitable methods to couple or attach the hardware component adjacent the first-shot are possible for example using a press-fit between the hardware component and the first-shot, insert molding the hardware component to the first-shot at the time the first-shot is initially molded, heat staking, attachment by a mechanical fastener, or by any other suitable method. It is the ability to withstand the overmold operation with proper positioning of the hardware component that defines if the hardware component is adequately coupled/attached to the first-shot.

The next operation 215 optionally involves loading the subassembly created in optional operation 210 onto a lead bore core pin pick-out. One way to accomplish the loading operation is to use a pick-out 140 that holds the assembly created in operation 210 and allows for its placement into a mating feature within the mold. Next, in optional operation 220, the lead bore core pick-out from the previous operation is loaded into the open mold 145. Other ways to load the assembly from 210 can be through the use of robotics or a mold that opens in a way to facilitate insertion of the assembly directly into the mold, such methods/operations would be in lieu of operations 210 and 215.

Next, in operation 225 the mold transitions from an open position to a closed position. There are many possible variations to how the mold may be devised to open and close. For example, with the use of cams and/or other mechanisms the mold may be designed to split apart from multiple directions different than discussed here. The closing or opening action of the mold sections can also occur simultaneously or in various sequences. However, regardless of variations in mold design, or the sequence that the various mold segments close, there is at least one pair of areas of the mold having contact areas that are opposing and that sandwich dedicated areas of the first-shot upon closing of the mold. This contact between the mold and the first-shot can be in the form of a line-to-line fit between the two components or the fit can be such that the first-shot is oversized in the area of contact with the mold and therefore the mold causes some compression onto the first-shot when the mold is fully closed. This holding of the first-shot by the mold allows the first-shot to be fixed in a rigid position during the overmold operation which has associated high pressures that are used to inject the overmold polymer. There may also be more then one clamp location such as a plurality of clamp locations that are designed into the first-shot and mold. In particular, multiple clamp locations may be useful in the creation of connector 102 that do not have any lead interconnects and therefore no leadbore first-shots to assist with holding the first-shot during overmolding.

Processing continues in operation 230 where molten thermoplastic material is introduced into the mold while the mold is held in a closed position, for example by using a press. This operation is referred to as overmolding. The aspects of the claimed invention, and how the first-shot is held within the mold, can apply to any one, of a number of overmolding operations. For example, it is possible for there to be multiple overmolding procedures such as a secondary overmold layer that is at least partially covered by a third overmold layer, or even further overmold operations beyond this. The molten thermoplastic material is generally introduced into the mold cavity at a high pressure, for example in the range of 12,000 to 15,000 psi. Due to the high pressure there is considerable turbulence that is generated within the mold cavity and considerable force applied to the first-shot upon injection of the polymer. The opposed holding of the first-shot by the mold helps to prevent movement of the first-shot and hardware components attached thereto during the turbulent introduction of the molten thermoplastic material. Once the mold is fully filled, pressure is typically maintained on the injected thermoplastic material to prevent or at least reduce any sink marks on the final component. In operation 235, the mold is cooled as the pressure on the injected thermoplastic material is generally maintained. Cooling can be accomplished by any acceptable method known by those skilled in the art of injection molding. In operation 240 the mold can be opened and the part removed or ejected from the mold. Generally operation 240 can be initiated once the injected thermoplastic material is adequately solidified. In the final operation 245 the ICR plate 117 and weld plate 110 can be trimmed by cutting at the ICR trim point 128. Note that operation 245 is optional depending on if the hardware component contained in the connector 102 includes an antenna or ICR and also depending on the design of those components.

Although the above description relates to a particular type of connector adapted to contain setscrew blocks, MBC, ICR, antenna, and with provision for the coupling of five leads, it may be noted that the invention may be utilized to produce any type of connector having any number or type of hardware components and that may or may not support the connection of medical leads. Thus, the above description and various embodiments of the specific connector set forth above should be considered merely exemplary in nature. These and other embodiments are within the scope of the following claims.

The invention claimed is:

1. A method comprising:
    (a) forming a first shot;
    (b) coupling at least one hardware component to the first shot to form a subassembly;
    (c) placing the subassembly between a set of opposing areas of a mold;
    (d) moving the set of opposing areas of the mold to directly contact and constrain the first shot of the subassembly within the mold with a clamping force; and
    (e) introducing a second shot over at least a portion of the subassembly to form an implantable medical device connector.

2. The method of claim 1, wherein the hardware component being an antenna and wherein a dielectric layer is formed over the antenna by the second shot.

3. The method of claim 1, wherein the hardware component is selected from the group consisting of a setscrew block, a multi-beam contact, an interconnect ribbon, an antenna, and a radiopaque identification tag.

4. The method of claim 1, wherein the first shot and the second shot polymer material being the same polymer material.

5. The method of claim 1, wherein the first-shot being formed of an injection molding process.

6. The method of claim 1, wherein the opposed areas of the mold contact the first shot in a location corresponding to a suture hole of the connector.

7. The method of claim 6, wherein the first shot and the second shot being the same thermoplastic material.

8. The method of claim 6, wherein the first shot being formed through an injection molding process.

9. A method comprising:
    (a) forming a first component with a portion of a suture hole therethrough;
    (b) coupling at least one hardware component to the first component to form a subassembly;
    (c) placing the subassembly between a set of opposing areas of a mold, the subassembly having an exposed clamping area;
    (d) moving at least one of the set of opposing areas to directly contact the clamping area; and
    (e) introducing a second shot over at least a portion of the subassembly to form a second component, the suture hole extending from a portion of the first component through a portion of the second component,
    wherein the first and second components form a connector for an implantable medical device,
    wherein a knit line delineates an interface between the first and the second components.

10. The method of claim 9, wherein the clamping area is tapered.

11. The method of claim 10 wherein the set of opposing areas of the mold constrain the subassembly in the tapered area of the clamping area.

12. The method of claim 9, wherein a leadbore opening is formed in the connector.

13. The method of claim 12, wherein the suture hole being perpendicular to the leadbore opening.

* * * * *